United States Patent [19]

Mayr et al.

[11] Patent Number: 5,094,850
[45] Date of Patent: Mar. 10, 1992

[54] PROCESS FOR THE PREPARATION OF INDUCERS OF NON-SPECIFIC IMMUNITY AND PRODUCT PRODUCED

[75] Inventors: Anton Mayr, Munich; Peter Thein, Oberzeitlbach; Walter Strube, Cologne, all of Fed. Rep. of Germany

[73] Assignee: Bayer Aktiengesellschaft, Leverkusen, Fed. Rep. of Germany

[21] Appl. No.: 256,009

[22] Filed: Oct. 7, 1988

[30] Foreign Application Priority Data

Oct. 17, 1987 [DE] Fed. Rep. of Germany ....... 3735277
May 11, 1988 [DE] Fed. Rep. of Germany ....... 3816139

[51] Int. Cl.$^5$ .................... A61K 39/12; A61K 39/275
[52] U.S. Cl. .................................... 424/89; 435/236; 435/238; 435/948
[58] Field of Search ................. 435/948, 236, 238; 424/89

[56] References Cited

U.S. PATENT DOCUMENTS

4,687,664  8/1987  Philapitsch et al. ............... 424/85

FOREIGN PATENT DOCUMENTS

0037441  10/1981  European Pat. Off.
86/00811  2/1986  PCT Int'l Appl.

OTHER PUBLICATIONS

Mayr, A. et al. 1986, J. Vet. Med. Ser. B 33 321–339.
Mueller-Bruneckert, G. et al. 1986, Comparison of the Effect of Viral Immunity Inducers PIND-AVI and ..., J. Vet. Med. Ser B 33 185–195.
Breiter, N. et al. 1985, Investigations on the Efficacy of the Paraimmunity Inactivated Avipoxvirus and PIND-ORF, Strahlentherapie 161 168–176.
Mayr, A. et al. 1986, Tierarztl Prax. 14 237–244.
Erfle, V. et al. 1983, Zentrabl Veterinaermed Reihe B 30 36–47.
Rubin, D. 1981, Immunologic Tolerance After Oral Administration of Reovirus: J. Immunol. 127: 1697–701.
Biological Abstracts, vol. 71, 1981, para. No. 52535, Philadelphia, PA, U.S.; P. Thein et al.: "Experiences with Using a Paramuniring Inducer PIND-AVI in Equine Practice", & Zentralbl Veterinaermed Reihe B 27(6): 499–512, 1980.
Biological Abstracts, vol. 73, 1982, Para. No. 75911, Philadelphia, PA, U.S.: P. Thein et al.: "Comparative Studies on the Activity of Paraimmunity Inducer Phytohemagglutinin PMITOGEN and Rhinopneumonites Virus on the Peripheral Leukocytes of the Horse", & Zentralbl Veterinaermed Reithe B 28(6): 432–449, 1981.

Primary Examiner—Sam Rosen
Attorney, Agent, or Firm—Sprung Horn Kramer & Woods

[57] ABSTRACT

Inducers of non-specific immunity are obtained by increasing the pH of a virus suspension of viruses which elicit non-specific immunity and then heating the pH-increased virus suspension. The pH value can be increased to between about 8 and 11 and heating is carried at temperature between about 50°–60° C.

9 Claims, No Drawings

PROCESS FOR THE PREPARATION OF INDUCERS OF NON-SPECIFIC IMMUNITY AND PRODUCT PRODUCED

BACKGROUND OF THE INVENTION

1. Field of the Invention

The present invention relates to a process for the preparation of inducers of non-specific immunity from viruses by a two-stage treatment which results in inactivation of the virus with, at the same time, lowering of the antigenicity but without destroying the non-specific immunizing activities.

2. Description of Related Art

According to A. Mayr, non-specific immunization means the acquisition of a rapidly developing protection, which is maintained for varying periods and is not pathogen- and not antigen-specific (paraspecific), of an individual against a plurality of quite different infections, toxins and antigens. The paraspecific protection (non-specific immunity) develops due to the stimulation of the paraspecific part of the cellular and humoral immune system.

Non-specific immunity may be acquired in a natural way during the course of an infection, or by treatment with inducers of non-specific immunity, immunomodulators, biological response modifiers (BRM) etc. Examples of known inducers of non-specific immunity are inactivated fowl pox, parapox or orthopox viruses [Tierärztl. Praxis 14, pages 237–244 (1986)].

Known inducers of non-specific immunity are inactivated by gamma rays, by heating or by chemical processes (DE-OS (German Published Specification) 2,714,665). A two-stage inactivation process has not until now been disclosed for the preparation of inducers of non-specific immunity.

The methods used are not new as techniques per se. However, they have been used in virology to date exclusively for other purposes. Zwartouw et. al. [J. gen. Microbiol. 38, 39–45 (1965)] made use of heat and alkalization to isolate precipitating antigens from vaccinia particles. These operations were not aimed at inactivation, they had the object of detecting antigens following different pretreatments of the starting material with serum, which contained antibodies against the complete virus, in the supernatant of the treated virus suspensions.

In the chosen system, these authors were able to demonstrate only that the antigen-antibody reaction taking place after the chemically thermal treatment of the vaccinia virus was quantitatively less distinct.

Experience to date with inducers of non-specific immunity from poxviruses and paramyxoviruses has shown that 2 criteria are important for the activity of inducers of this type:

1. inactivation under mild conditions and 2. a reduction in the total antigenicity with, at the same time, retention of the non-specific immunizing activities.

SUMMARY OF THE INVENTION

It has been found that inducers of non-specific immunity are obtained by adjusting the pH of virus suspensions of viruses which elicit non-specific immunity to values between 8 and 11, and then heating at 50°-60° C. for 40-120 minutes.

It is surprising that by a combination of alkalization and heating not only is the requirement for inactivation of the viruses and reduction in the total antigenicity with retention of the non-specific immunizing activities met in an optimal manner, but this additionally gives rise to advantages for the preparation of inducers of non-specific immunity. These are:

1. The inactivation process is straightforward to carry out without exposure to radiation or toxic chemicals.

2. The diminished antigenicity means that the risk of sensitization after repeated use is diminished.

3. The economics are improved owing to the simplification of the preparation process.

DESCRIPTION OF THE PREFERRED EMBODIMENTS

The process is carried out by adjusting the pH of the virus suspension to values between about 8-11, preferably between about 9-10.

The adjustment is carried out with aqueous inorganic alkali metal hydroxides such as, for example, sodium or potassium hydroxide, carbonates such as, for example, sodium or potassium carbonate, or bicarbonates such as, for example, sodium or potassium bicarbonate.

Thermal inactivation is then carried out by heating to about 50°-60° C. for 40-120 minutes, and heating at 55°-60° C., especially at about 56° C., for 60-120 minutes, is preferred.

The procedure for the inactivation is particularly preferably at about pH 10 and at about 56° C. for about 60-120 minutes.

Virus species for the preparation of inducers of non-specific immunity, for which the inactivation according to the invention is particularly suitable, and which may be mentioned are:

Poxviruses, especially of the genus avipox, particularly preferably of the species gallinae, attenuated immunization strain HP-1,438. Passage in chicken embryo fibroblast cultures (FHE). (The strain is disclosed in, for example, Collegium Veterinarium 1978, pages 35 et seq. The virus strain is deposited under the deposition name "Mayr-Stickl Avipox Interferon Inducer" at the Landesimpfanstalt Nordrhein-Westfalen, Abteilung Viruszüchtung und -prüfung. It is available for release to the public.); of the genus parapoxvirus particularly preferably the species orfvirus, the attenuated strain C 1701, 138. Passage in lamb kidney or embryonic bovine bovine lung cultures (the strain ORF D 1701 is disclosed, for example, in Tierärztl. Praxis 14, 237-244 (1986); laboratory designation for the inducer of non-specific immunity prepared therefrom: PIND-ORF. The strain was deposited as immunization strain at the Bayerischen Landesimpfanstalt, Am Neudeck 1, 8000 Munich 95, on Sept. 1, 1981). The strain was deposited on Apr. 4, 1988 at the Insitut Pasteur, Collection Nationale de Cultures de Microorganismes, 25 rue du Docteur Roux, 75724 Paris, under the name CNCM I-751; of the genus orthopoxvirus particularly preferably the species vacciniavirus, the attenuated strain MVA, 530. Passage of vacciniavirus CVA in FHE cultures the strain MVA is described by A. Mayr in Zbl. Bakt. Hyg. I. Abt. Orig. B, 167, 367 (1978). It has been approved for preliminary immunization against human smallpox by the Paul-Ehrlich Institute, Frankfurt, and is deposited in the Institute of Microbiology, Dusseldorf.

However, other virus species are also suitable for the preparation of inducers of non-specific immunity using the inactivation according to the invention, such as, for example, paramyxoviruses, reoviruses and herpesviruses.

The viruses are initially grown in a manner known per se on suitable cell cultures, for example on cell cultures of mammalian or avian tissue cells. It is possible for this to be carried out in monolayer cell cultures or suspension cultures or in an incubated chicken egg.

The nutrient media used for the monolayer or suspension cultures are the known media, for example those of Earle, Eagle or Hanks.

The virus is harvested and, where appropriate, purified by known processes. The virus harvest is then subjected to the inactivation process according to the invention.

The inactivated virus harvest is subsequently cooled or freeze-dried and stored or used for the preparation of an inducer of non-specific immunity. This entails the preparation of products which can be administered via the mucosa, for example orally or intranasally, and parenterally, for example intramuscularly or subcutaneously.

The inducers of non-specific immunity prepared as in the examples which follow might be freeze-dried and are used in this form as starting materials for the preparation of appropriate medicaments. Before the lyophilizate is used it is mixed, appropriate for the starting volume, with customary pharmaceutical vehicles, preferably with sterile pyrogen-free distilled water. The preparation in this form is suitable both for parenteral (for example intramuscular or subcutaneous) and for topical administration.

The inducers of non-specific immunity can also be incorporated in other pharmaceutical vehicles. In this connection, care must be taken that the sterility and stability are not impaired, for example by proteolytic constituents of the vehicle.

In prophylaxis, inducers of non-specific immunity are administered once to 3 times at intervals of 24 hours. On therapeutic use, 1 to 3 treatments per day are carried out for 3 to 5 days depending on the severity of the disease. The dose depends on the size of the relevant species and on the administration form (for example cattle parenteral: 4 ml; pup (dog) parenteral: 0.5 ml).

EXAMPLE 1

The starting material used is the attenuated, plaquepurified (3 passages) fowl pox virus strain HP-1 in the 441st culture passage in chicken embryo fibroblast cultures (FHE) with an infectiosity titre of $10^{7.5}$ $CID_{50}$/ml. Earle's MEM with an addition of 3% foetal calf serum is used for cultivation of the FHE cultures, and Earle's MEM without additions is used as maintenance medium (virus medium). The virus material is used to inoculate about 90%-continuous FHE monolayer cultures (for example 200 ml of medium and 0.5 ml of virus suspension per Roux dish). About 24 hours after infection, or when 80-100% of the cell culture has undergone the virus-specific change (granulation, rounding and detachment, lysis of the cells), the cell lawn which is still present is detached by shaking the cultures, and the virus and the cell-containing medium are treated with ultrasound (Branson Sonifier 15 min) in order to disrupt the cells which are still intact. The cell detritus is then removed by low-speed centrifugation.

Samples, are taken of the virus harvest to check the sterility and infectivity. Only virus harvests which are free of contaminations (viruses, bacteria, fungi, mycoplasmas) and have an infectiosity titre of at least $10^{7.25}$ $CID_{50}$/ml are used further. Harvests which do not meet these requirements are discarded.

The virus harvest is stored at $+4°$ or $-60°$ C. until used further.

The virus material is heated to $37°$ C. before the start of the two-stage inactivation. In the first stage of inactivation, the virus suspension is adjusted to a pH of 10.0 with 1N NaOH. The alkalized suspension is then immediately placed in a waterbath at $56°$ C. Continuous mixing of the virus suspension using a magnetic stirrer, and of the water bath using a customary stirrer, is carried out to achieve uniform mixing and heating. The thermal inactivation is carried out for 60 minutes.

After this time, subsequent passages are carried out to demonstrate that no residual infectiosity is any longer detectable.

The inducer of non-specific immunity obtained in this way is called PIND-AVI' (therm.) and is stored at temperatures of $+4°$ C. or $-60°$ C. It can also be stored in freeze-dried form.

The purity, specificity and innocuousness of the PIND-AVI' inducer of non-specific immunity obtained according to the invention are examined by appropriate control investigations.

The testing for the specificity, purity and innocuousness meets the requirements of the European Pharmacopoeia in the following criteria:

1. A check by electron microscopy using the customary methods show large numbers of typical pox particles, some of which are empty, in the product. It is free of other microbial structures.

2. The customary checks for microbial contamination show that the product is free of other viruses, bacteria, fungi and mycoplasmas.

3. The toxicity, teratogenicity and pyrogenicity were tested as specified in the European Pharmacopoeia, and no positive results were found.

4. A check of the content of remaining non-inactivated virus: this entails the finished inducer of non-specific immunity being subjected in the customary manner to a titration in FHE tube cultures, and the infectiosity titre being determined by means of the cythopatic effect which occurs. The residual virus content in a further 3 subsequent passages is 0.

To demonstrate the activity, the inducer of non-specific immunity is examined by the following method:

The VSV infection model in the baby mouse is used as in vivo demonstration [J. Vet Med. B, 33, 321-339 (1986)]. It can also be used to determine the effective units (EU/ml).

Table 1 shows the titration of the activity of a PIND-AVI' in the VSV model. A titration of this type is used to determine the effective units (EU/ml) in a batch: the dilution stage at which an effect index of at least 20 is still reached contains 1 EU per 0.1 ml (injection dose/per mouse) or 10 EU/ml (in Example: 1: 16 final titre; the batch contains 160 EU/ml.).

TABLE 1

Titration of the non-specific imunogenic activity of PIND-AVI' in the VSV infection model

| Product | Dilution stage | Effect index |
| --- | --- | --- |
| PIND-AVI' | 1:4 | 48 |
| | 1:8 | 45 |
| | 1:16 | 34 |
| | 1:32 | 13 |

In vitro demonstration of the activity of the inducer of non-specific immunity according to the invention entails 1. use of the activity of peritoneal NK cells 24 hours after treatment with PIND-AVI' in the 4-hour chromium-51 release test [J. Vet. Med. B, 33, 321-339 (1986)]. For this purpose, 0.2 ml of PIND-AVI' is administered to mice 24 hours before the cells are obtained. The results of this test show a dose-dependent stimulating effect of PIND-AVI'.

In an in vitro test, the effect of PIND-AVI' on the colony-stimulating activity in the serum of mice 8 hours after the treatment is tested. The results of this CSA test show a dose-dependent stimulating effects of PIND-AVI'.

EXAMPLE 2

The starting material used for the preparation of an inducer of non-specific immunity is the attenuated Parapox-virus ovis (ORF, ecthyma of sheep), strain D 1701, in the 138th culture passage (infectiosity titre: $10^{7.75}$ $CID_{50}$/ml) in lamb kidney or embryonal bovine lung cultures. The virus harvests are prepared and inactivated as in Example 1, but with an extended thermal inactivation of 2 hours. After about 2 hours complete inactivation or virus infectiosity is achieved.

The tests of the purity, innocuousness, specificity and activity are carried out as described in Example 1. The results achieved are the same as in Example 1.

EXAMPLE 3

The inducer of non-specific immunity is prepared, and it is tested for purity and activity, as in Example 1, but using the attenuated Orthopoxvirus commune, Vaccinia virus, strain MVA. The virus inactivated by this process has non-specific immunizing properties.

EXAMPLE 4

The inducer of non-specific immunity is prepared, and it is tested for purity and activity, as in Example 1, but using the lentogenic Newcastle desease virus (paramyxovirus), strain Hitchner $B_1$. The virus inactivated by this process has non-specific immunizing properties.

EXAMPLE 5

The inducer of non-specific inactivity is prepared, and it is tested for purity and activity, as in Example 1, but using the reovirus serotype 3. The virus inactivated by this process has non-specific immunizing properties.

EXAMPLE 6

In order to demonstrate the possible uses and the activity of the inducer of non-specific immunity prepared as in Example 1, examples of the therapeutic and prophylactic use are compiled in Tables 2 and 3 which follow.

The use of PIND-AVI' in a double-blind trial on pregnant bitches and their litters shows clearly that effective control of infectious fading, which is characterized as a rule by high mortality in the first week of life, is possible by prophylactic use of this product (Table 2).

The double-blind trial in a calf-fattening farm, in which treatment with PIND-AVI' was carried out immediately after the calves were received in the fattening farm (2×4 ml each time, i.m. at an interval of 24 hours), shows clearly that the product has an excellent prophylactic activity against infections of various origins.

As is evident from the data, it is possible by use of the inducer of non-specific immunity to stop or ameliorate the progress, or entirely to prevent the onset, of infectious diseases of various origins.

They further demonstrate the innocuousness of the inducers of non-specific immunity according to the invention. No side effects were observed.

TABLE 2

Efficacy of PIND-AVI' in the prophylaxis of infectious fading

| Clinical picture and number of treated cases | Mode of treatment | Results |
| --- | --- | --- |
| 42 newborn puppies from 10 litters; treated | Dam in the last week of pregnancy; 2 × 1 ml i.m. Newborn puppies: 0.5 ml each i.m. 1. immediately after delivery 2. 12–24 hours after delivery | all 42 puppies reared healthy |
| 18 untreated litter siblings | | 6 reared, 12 died within the first week of life |

TABLE 3

Efficacy of PIND-AVI' in the prophylaxis of crowding disease in calf fattening

| Trial group | Unwell calves | Dead calves |
| --- | --- | --- |
| 32 calves, PIND-AVI'-treated | 2 | 0 |
| 32 calves, untreated | 15 | 4 |

What is claimed is:

1. A process for the preparation of an inducer of non-specific immunity comprising inactivating a virus suspension of avipox viruses, parapoxviruses, paramyxoviruses, reoviruses, or inactivated virus suspension obtained from the inactivation process according to claim 1.

2. A process according to claim 1, wherein the virus suspension which is inactivated contains a parapoxvirus of the species orfvirus or stomatitis papulosa virus.

3. A process according to claim 1, wherein the pH of the virus suspension is increased to a pH between about 9 and 10 and the heating is carried out at temperatures between about 55° and 60° C. for a period of from about 60 to 90 minutes.

4. A process according to claim 1, wherein the virus suspension to be inactivated contains fowl pox viruses.

5. A process according to claim 1, wherein the virus suspension to be inactivated contains paramyxoviruses or reoviruses.

6. An inducer of non-specific immunity, which is the inactivated virus suspension obtained from the inactivation process according to claim 2.

7. An inducer of non-specific immunity, which is the inactivated virus suspension obtained from the inactivation process according to claim 4.

8. An inducer of non-specific immunity, which is the inactivated virus suspension obtained from the inactivation process according to claim 5.

9. An inducer of non-specific immunity, which is the herpesviruses by increasing the pH of the virus suspension to a pH between about 8 and 11 and thereafter heating said pH-increased virus suspension at a temperature between about 50° to 60° C. for a period between about 40 to 120 minutes thereby inactivate the virus, and lower antigenicity, but without destroying non-specific immunizing activity.

* * * * *

UNITED STATES PATENT AND TRADEMARK OFFICE
CERTIFICATE OF CORRECTION

PATENT NO. : 5,094,850

DATED : March 10, 1992

INVENTOR(S) : Mayr et al.

It is certified that error appears in the above-identified patent and that said Letters Patent is hereby corrected as shown below:

Col. 6, lines 37-39  Delete " inactivated virus suspension obtained from the inactivation process according to claim 1. " and substitute -- herpesviruses by increasing the pH of the virus suspension to a pH between about 8 and 11 and thereafter heating said pH-increased virus suspension at a temperature between about $50°$ to $60°C$ for a period between about 40 to 120 minutes to thereby inactivate the virus, and lower antigenicity, but without destroying non-specific immunizing activity --.

Col. 6, claim 9 lines 2-8  Delete " herpesvirused by increasing the pH of the virus suspension to a pH between about 8 and 11 and thereafter heating said pH-increased virus suspension at a temperature between about $50°$ to $60°C$. for a period between about 40 to 120 minutes thereby inactivate the virus, and lower antigenicity, but without destroying nonspecific immunizing activity " and substitute -- inactivated virus suspension obtained from the inactivation process according to claim 1. --

Signed and Sealed this

Twenty-first Day of December, 1993

Attest:

BRUCE LEHMAN

*Attesting Officer*    *Commissioner of Patents and Trademarks*